(12) United States Patent
Lähdesmäki

(10) Patent No.: US 6,553,251 B1
(45) Date of Patent: Apr. 22, 2003

(54) METHOD AND ARRANGEMENT FOR HEARTBEAT DETECTION

(75) Inventor: Tapani Lähdesmäki, Oulu (FI)

(73) Assignee: Polar Electro Oy, Kempele (FI)

( * ) Notice: Subject to any disclaimer, the term of this patent is extended or adjusted under 35 U.S.C. 154(b) by 267 days.

(21) Appl. No.: 09/705,528

(22) Filed: Nov. 2, 2000

(30) Foreign Application Priority Data

Nov. 5, 1999 (FI) .............................................. 19992398

(51) Int. Cl.⁷ .......................................... A61N 5/0402
(52) U.S. Cl. ................................................... 600/519
(58) Field of Search ........................ 600/509, 519–521; 128/901–903

(56) References Cited

U.S. PATENT DOCUMENTS

| | | | | |
|---|---|---|---|---|
| 5,307,818 A | * | 5/1994 | Segalowitz | 128/903 |
| 6,149,602 A | * | 11/2000 | Arcelus | 600/509 |
| 6,289,238 B1 | * | 9/2001 | Besson et al. | 128/903 |

FOREIGN PATENT DOCUMENTS

| | | |
|---|---|---|
| EP | 0 760 224 A1 | 3/1997 |
| EP | 0760224 A1 | 3/1997 |
| FI | 100452 B | 12/1997 |
| FI | 101191 B | 5/1998 |
| GB | 2114889 A | 9/1983 |
| GB | 2 114 889 A | 9/1983 |
| WO | WO97/48333 | 12/1997 |
| WO | WO 97/48333 | 12/1997 |

OTHER PUBLICATIONS

European Search Report dated Feb. 20, 2001.

* cited by examiner

*Primary Examiner*—Jeffrey R. Jastrzab
(74) *Attorney, Agent, or Firm*—Hoffmann & Baron, LLP

(57) ABSTRACT

An arrangement for heartbeat detection, the arrangement comprising a first measuring device (202) for measuring the heart rate signal of a person on the skin of the person in a first measuring area, a second measuring device (204) for measuring the heart rate signal (204A) of a person on the skin of the person in a second measuring area simultaneously with the measurement made in the first measuring area, which first measuring device (202) comprises a transmitter (756) for transmitting the timing information (104A) formed in the first measuring area to the second measuring device (204), which second measuring device (204) comprises a receiver (714) for receiving the timing information (104A) transmitted from the first measuring device (202), which second measuring device (204) comprises a detection means (718) for detecting the heartbeat by means of the heart rate signal (204A) measured in the second measuring area and the timing information (104A) received from the first measuring device (202).

41 Claims, 7 Drawing Sheets

METHOD AND ARRANGEMENT FOR HEARTBEAT DETECTION

BACKGROUND OF THE INVENTION

1. Field of the Invention

The invention relates to a method and heart rate monitoring equipment for heartbeat detection on the basis of a heart rate signal.

2. Brief Description of the Related Art

A heart rate monitor is a device used in sports and medical science, by means of which it is possible to monitor heart functions, such as rate, standard deviation of heartbeat intervals or other corresponding heart rate information. With reference to FIG. 2, heart rate monitors are constructed in such a manner, for instance, that they comprise an electrode belt 202 which is placed on the chest of a person 200 and measures the heart rate, the heart beats measured by the belt being transmitted wirelessly or through a conductor to a receiver unit 204 strapped to the wrist. Further, heart rate monitors can be constructed in such a manner that the entire heart rate monitoring equipment 204 is strapped to the wrist, from which the heart rate is measured using either an electric signal generated by a heart beat or changes in blood vessel pressure. The heart rate monitoring equipment can also be located in its entirety on the chest, in which case any required displays and memory units are in an apparatus 202 located on the chest.

The operation of a heart rate monitor is based on the fact that the heart when contracting generates a series of electric pulses which can be measured everywhere in the body, thus also in the hands and fingers. The signal is called an EKG signal. It is possible to identify sections of the different functional cycles of the heart from-this signal, as shown in FIG. 1. The figure shows the electric signal 100 generated by one heart beat on a time-signal strength level 108. The Y axis shows the signal strength (P) 106 as a function of the time (T) 104 shown on the X axis. The signal can be divided into peaks, 102A to 102E, of which the cardiogram feature that is easiest to distinguish, the QRS complex (102B–102C–102D), is generated by the contraction of the ventricles. The time instant corresponding to an R peak 102C of the cardiogram 100 is marked at time instant 104A.

The amplitude of a typical EKG signal is 1 to 2 mV measured from the chest at a good electrode contact, but if the skin is dry, it can be as low as 200 $\mu$V. Measured from a finger or hand, the signal is much weaker than this. The most reliable heart rate measurement is obtained by QRS complex detection from an EKG signal, because it contains the highest amount of energy and its spectrum differs sufficiently from the spectrum of movement artefacts. When the heart rate increases as a result of strain, the duration and amplitudes of the features of an EKG signal remain nearly unchanged in a healthy person and only the distance from a P wave to the next P wave becomes shorter. The EKG spectrum contains the most significant frequency components from 2 Hz to approximately 20 to 30 Hz. The peak of the QRS complex is in the frequency range of 10 to 15 Hz. Most disturbances in heart rate measurement are caused by movement artefacts, and to minimize these disturbances, the electrode contact must be appropriate and the electrode material must be selected correctly. The spectrums of P waves, T waves and movement artefacts are in the frequency range of 1 to 5 Hz, which is below the frequency range of the QRS complex and thus easy to filter away. Disturbances caused by muscle movement disturb the measurement, because the spectrum of an EMG signal partly overlaps that of the EKG signal. EMG disturbances can be eliminated or significantly reduced by filtering the frequencies in question away from the EKG spectrum and by moving the electrodes away from large muscles which do not exist in hands. 50 Hz (60 Hz) network interference only occurs outdoors in the immediate vicinity of high-voltage lines. Indoors, network interference may disturb the measurement in hospitals and sports halls, for instance. This interference can be reduced with a band-stop filter without attenuating the frequency components of the actual EKG signal.

The heartbeat signal measured by wrist-held heart rate monitoring equipment from an electric signal or pressure pulse of the heart is thus weak and disturbed by electric signals generated by muscle movement. Present apparatuses are trained by means of a computer program, for instance, to identify the format of a QRS complex. The heart rate monitor must first collect the EKG signal of the user and the data is then downloaded into a computer. On the computer, a QRS complex is selected from the EKG signal and transmitted back to the heart rate monitor as a QRS model. Prior art solutions contain significant drawbacks. Known heart rate monitors which measure heart rate from the wrist require computer operations and additional work when the QRS complex is separated from the EKG data. Another drawback is that heart rate monitors require bidirectional telecommunications with the outside world.

SUMMARY

It is an object of the invention to implement an improved method for detecting heartbeat. This is achieved by the method described in the following. It is a method for heartbeat detection measuring the heart rate signal of a person from the person's skin in a first measuring area, measuring the heart rate signal of the person from the person's skin in a second measuring area simultaneously with the measurement made in the first measuring area, transmitting timing information formed of the heart rate signal measured in the first measuring area to a part of a device in the second measuring area, detecting the heartbeat by means of the heart rate signal measured in the second measuring area and the timing information received from the first measuring area.

The invention also relates to an arrangement for heartbeat detection. The arrangement comprises a first measuring device for measuring the heart rate signal of a person on the skin of the person in a first measuring area, a second measuring device for measuring the heart rate signal of a person on the skin of the person in a second measuring area simultaneously with the measurement made in the first measuring area, which first measuring device comprises a transmitter for transmitting the timing information formed in the first measuring area to the second measuring device which comprises a receiver for receiving the timing information sent from the first measuring device, and which second measuring device comprises detection means for detecting the heartbeat by means of the heart rate signal measured in the second measuring area and the timing information received from the first measuring device.

The invention also relates to a heart rate monitor for heartbeat detection. The heart rate monitor comprises one or more means for measuring a heart rate signal on the skin of a person, a receiver for receiving timing information related to the heart rate signal, detection means for heartbeat detection by means of the measured heart rate signal and the received timing information.

Preferred embodiments of the invention are set forth in the dependent claims.

The invention relates to heart rate monitors which measure the heart rate of a person during the actual measurement in an area of a weak heart rate signal. In this context, an area of a weak heart rate signal refers to other areas than the chest which in this application is called an area of a strong heart rate signal. An area of a weak heart rate signal refers, for instance, to the wrist of a person, even though the invention is not limited to using the wrist as the measuring area. Measuring a heart rate signal from the wrist or a corresponding location can be done in several different ways, such as by measuring the electric signal generated by a heart beat, by measuring a pressure pulse generated by a heart beat in a blood vessel, or by monitoring the changes in the transmission of light in tissue caused by blood circulation. In electric measurement, a first sensor, i.e. electrode, of the heart rate monitor is held against the left hand, for instance, and one of the right hand fingers is made to touch a second electrode to achieve a potential difference. The basic principle of the invention is that the heart rate monitor is trained to identify from a heart rate signal measured in a weak heart rate signal area a signal peak, for instance an R peak of a signal, using timing information measured in a strong heart rate signal area. The measurement in the strong heart rate signal area takes place simultaneously with the measurement in the weak heart rate signal area, and timing information refers here preferably to a peak in a heart rate signal, such as an R or S peak, but the timing information may also comprise a combination of the time instants of several peaks, for instance. In such a case, information is sent from the strong heart rate signal area to a part of a device in the weaker heart rate signal measurement area always when an R peak, for instance, is detected in the EKG signal. It is then possible to locate the R peak from the measured signal in the weaker heart rate signal area. If the measurement in the weak heart rate signal area is made as a pressure measurement or optically, a maximum point, for instance, is identified in the pulse, the maximum point being an R peak corresponding to an electric signal. The method described above, in which a heart rate monitor used in a weak heart rate signal area is trained to interpret the heart rate signal, is called a training phase in the description of the invention. A using phase refers to measuring the heart rate signal in the second measuring area without external timing obtained from the first measuring area.

According to an embodiment of the invention, a measuring wave format is formed in the weak heart rate area, i.e. the second measuring area, in such a manner that the heart rate signal is read from the received timing time instant onward and backward for a given time, and the obtained heart rate signal sequence is stored in the memory buffer. The heart rate signal sequence is read from the memory buffer and compared with a wave model selected in advance. The wave model can be selected either for an entire PQRST complex or for only a part of it. Since it is known that QRS complexes are unique and may differ from each other quite a lot, several wave models of different formats should preferably be available. The wave model can, for instance, be selected for the first time in such a manner that a wave model which provides the best correlation with the measuring wave format is selected from the wave models. Because the measuring wave format and the wave model will probably not correlate perfectly at the first time, a combination wave of the above-mentioned waves is formed by averaging said waves, for instance. After this, the wave model is replaced with the formed combination wave. This is then repeated until the correlation of the wave model and the measuring wave format is sufficiently high to make the wave model good enough to depict the heart rate signal measured in the second measuring area, and after this, the wave model is selected as the comparison wave format.

During the using phase of the heart rate monitor, the measuring wave formats are preferably compared with a comparison wave format formed as described above, and when their correlation exceeds a pre-set criterion, the measuring wave format is accepted as a heart beat.

One preferred device configuration of the invention for the training phase is to have a transmitter electrode belt on the chest and a receiver unit, i.e. a wrist gauge, on the wrist. The timing information measured by the transmitter electrode belt is transmitted inductively, optically, over a connecting line or in another corresponding manner to the wrist gauge. During the using phase, the transmitter electrode belt is no longer needed, and the heart rate is measured only using the wrist gauge, i.e. heart rate monitor. The method described above and the equipment implementing the method make it possible to optimize the detection of the heart rate signal of one user. Because the heart rate signals of different persons differ from each other, the device must be trained to detect heartbeat separately for each user.

The invention provides the advantage that heartbeat detection in a weak measuring area and thus also measuring the heart rate can be considerably improved by means of the timing information obtained during the training phase from the strong measuring area.

BRIEF DESCRIPTION OF THE FIGURES

In the following the invention will be described in greater detail with reference to the attached drawings in which.

DETAILED DESCRIPTION OF THE INVENTION

In the following, the invention will be described by means of preferred embodiments and with reference to the attached FIGS. 3 to 8. First, a preferred embodiment of the invention is described with reference to FIGS. 3A and 3B. In the starting step 300 of the method, an electrode belt 202 has been placed in a first measuring area of a person 200, preferably the chest. A second measuring area, which preferably is the person's wrist, has a receiver unit 204. The electrode belt 202 preferably comprises transmitter electronics for transmitting timing information to the receiver unit 204 which comprises receiver electronics for receiving the timing information. In method step 302, the heart rate signal of the person 200 is measured in the first measuring area.

Figure 1:
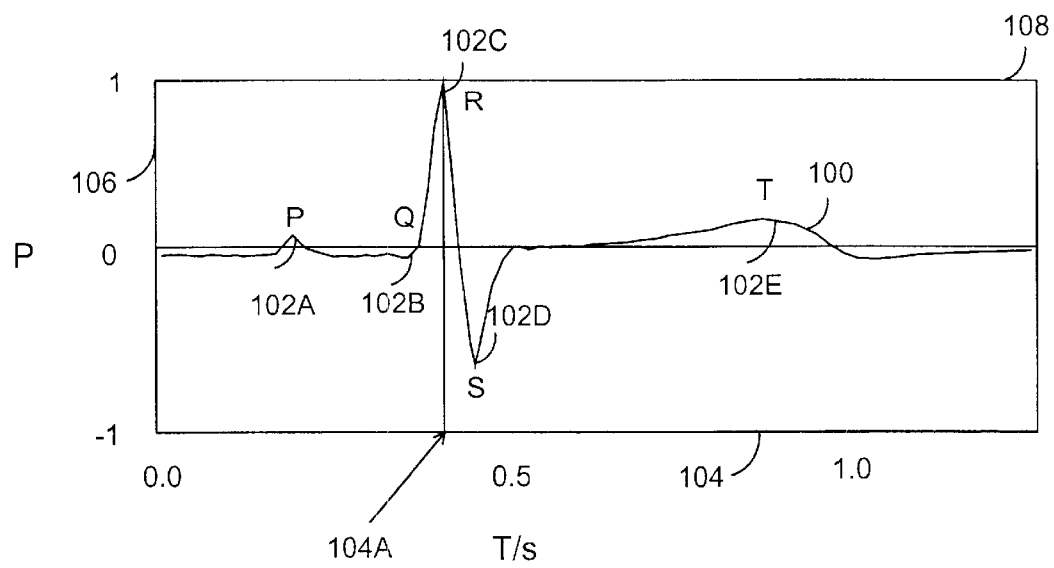
FIG. 1 shows a presentation format of an electric signal formed from a heart beat.
Figure 2:
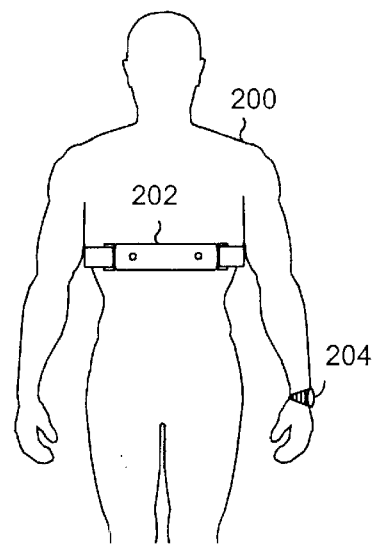
FIG. 2 shows a person using a heart rate monitor.

Simultaneously with the measurement in step 302, the heart rate of the person 200 is, in step 304, measured in the second measuring area. In step 306, the timing information on the heart rate signal is transmitted to the second measuring area. According to a preferred embodiment, the transmitter electrode belt 202 transmits inductively one or more magnetic pulses always when it detects an R peak in the heart rate signal, i.e. in FIG. 1, at the time instant 104A. In step 308 of FIG. 3A, the heartbeat is detected on the basis of the timing information received in the second measuring area and the heart rate signal measured in the second measuring area.

Figure 3A:
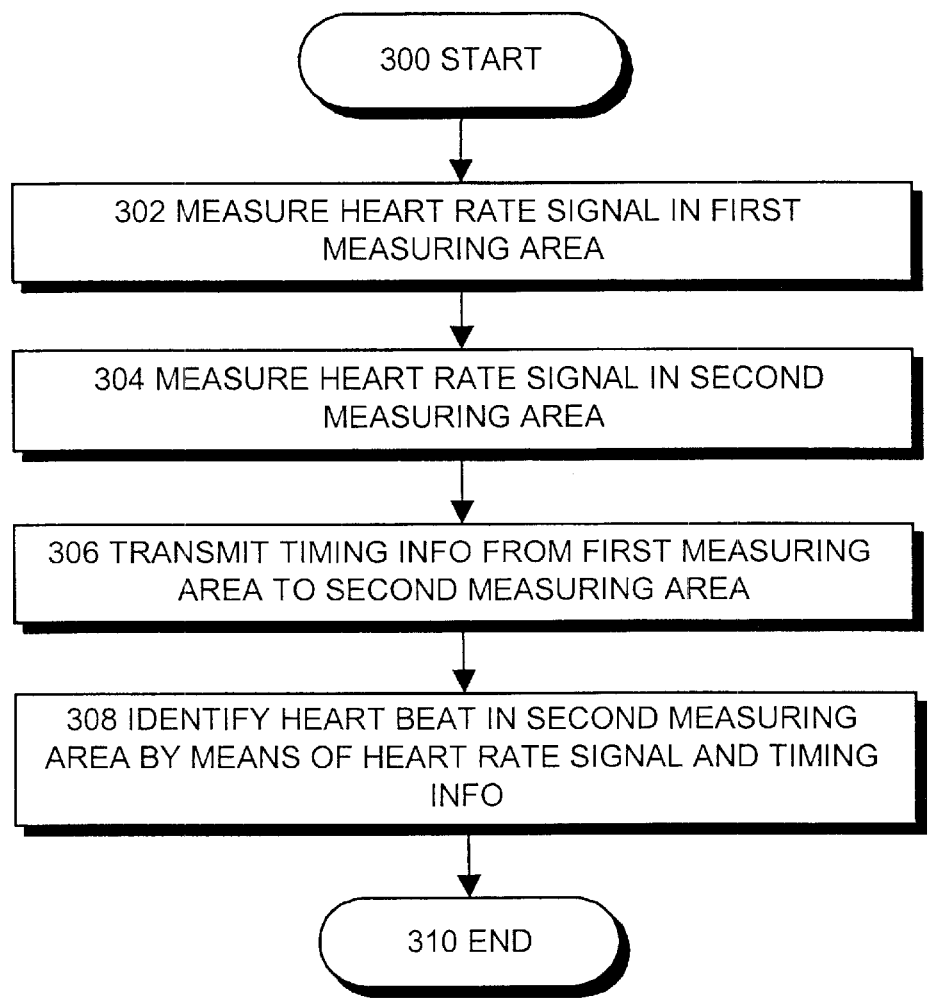
FIGS. 3A and 3B show a preferred embodiment of the method of the invention.
Figure 3B:
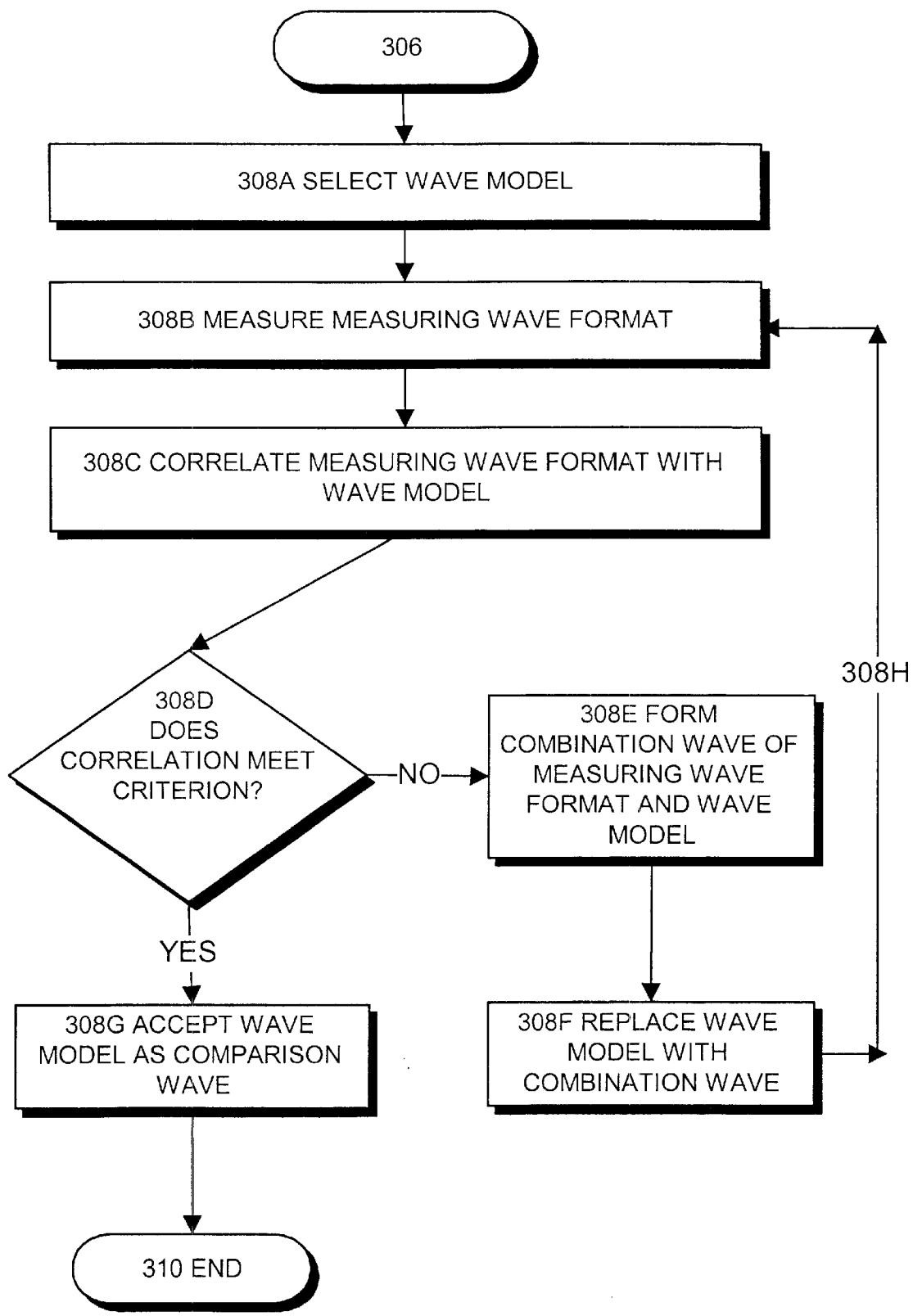

FIG. 3B shows a preferred embodiment of step 308 in more detail. In step 308A, a wave model is selected, from which an iteration toward a comparison wave to be formed will be started. A comparison wave refers herein to a wave format used as basis for comparison when the heart rate monitor is used, i.e. after the training phase. Step 308B shows that during the training phase, a measuring wave format generated by a heart beat is measured in the weak heart rate area. In step 308C, the measuring wave format is correlated with the selected wave model. First time, the comparison can naturally also be done in such a manner that there are several wave models to select from and the one having the best correlation with the measuring wave format is selected. A threshold value is preferably set to the correlation between the measuring wave format and the wave model, for instance requiring that the waves correlate in 90 percent. In step 308D, a check is made to see whether the above-mentioned threshold value was met and if it was, the wave model is accepted as a comparison wave in step 308G, and the measuring wave formats generated by a heart beat are compared to this comparison wave during the using phase of the heart rate monitor.

If the threshold value was not met in step 308D, a new iteration round is required to improve the wave model to achieve an acceptable comparison wave. In step 308E, a combination wave format of the measuring wave format and the wave model is formed. The combination wave is preferably formed as an average of said waves, but it is obvious that in forming the combination wave it is also possible to weigh more the wave model, for instance, in which case the wave model does not change too much due to the influence of one measuring wave. In step 308F, the used wave model is replaced by the formed combination wave. In a preferred embodiment, the replacement of the wave model by the combination wave is only done if the correlation of the measuring wave and the wave model has met a certain set criterion, for instance that the correlation between the above-mention waves must be at least 60%. This way, the situation is avoided that a completely different measuring wave format and wave model were combined to form a new wave model. After this, the routine returns from step 308H to method step 306B in which the measuring wave format corresponding to a new heart beat is read, and the above-mentioned steps are performed to it until in step 306D, the correlation between the measuring wave format and wave model meets the condition set to it.

Figure 4:
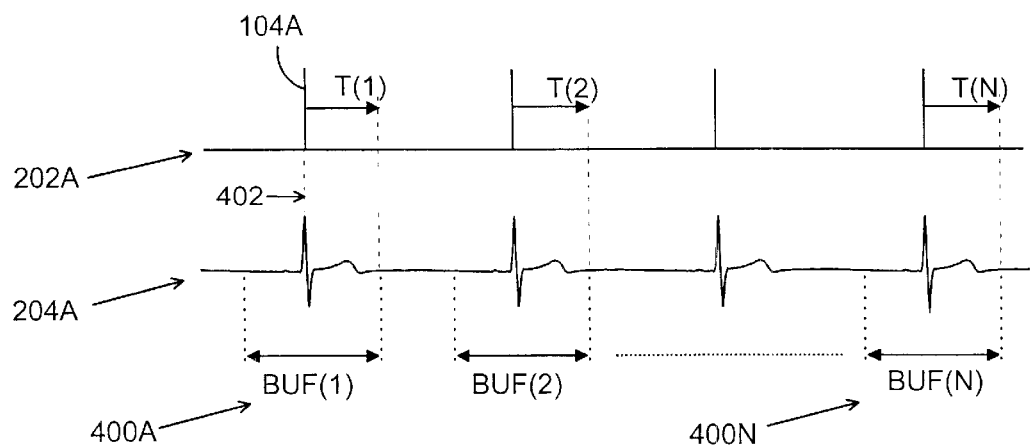
FIG. 4 shows the timing of a heart rate signal on the basis of another heart rate signal.

FIG. 4 shows an embodiment of the timing of the invention. On top, the figure shows a timing signal 104A formed of the heart rate signal 202A measured on the chest and at the bottom, a heart rate signal 204A measured in a weaker heart rate signal area. The time instant 104A corresponding to the R peak of the heart rate signal measured on the chest is transmitted using a wireless connection 402, for instance, to a receiver strapped to the wrist, for instance, where the time instant is matched with the R peak of the signal measured on the wrist. It is obvious to a person skilled in the art that when the signal is measured on the chest, processed and the timing information is transmitted to the receiver, there is a slight delay which the receiver must take into account when locating the R peak. The receiver reads a time T(1) forward and backward of the received time instant 104A, whereby a time 2*T(1) of the read signal is stored in the buffer BUF(1) 400A. The heart rate signal stored into the buffer 400A can naturally contain a longer period of the signal onward from the time instant than backward, or vice versa. The electric signal generated by a heart beat lasts approximately 160 ms, so the time T(1) can be approximately half of this. The signal sample corresponding to the second received timing information is read in the second measuring area and stored into the buffer BUF(2) and so on until the last heart rate signal sequence to be measured is stored in the buffer BUF(N).

Figure 5:
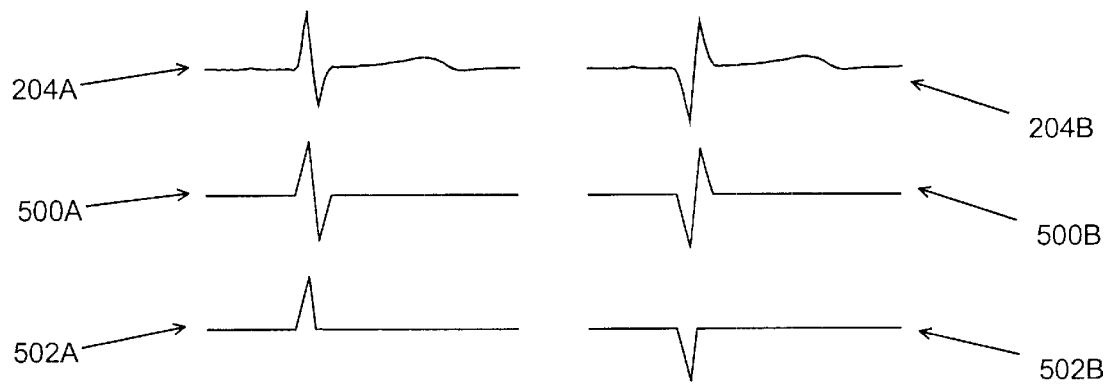
FIG. 5 shows the comparison of a heart rate signal to wave models of a signal.

FIG. 5 illustrates a situation of the method described in FIG. 3B. The signal measured in the weaker heart rate signal area is marked with 204A/204B:. The signal 204A is measured from a different person than the signal 204B. The signals show the differences in the heart rate signals of different persons. The correlation according to method step 308C is preferably performed so that the wave model corresponding to the signal 204A is obtained from a wave model like the wave model 500A. Correspondingly, the best correlation for the signal 204B with a wave model is reached with a wave model like the model 500B. The wave models 502A/502B are slightly simplified embodiments of wave models as compared with the models 500A/500B. The comparison wave model obtained as a result of the iteration is stored in the memory buffer BUF(X) described in FIG. 6, and the wave model in the buffer forms itself gradually in the format of the actual QRS complex of the user, and the device achieves an optimal operation. The action between the new heart rate signal and model can, for instance, be repeated twenty times, in which case the format of the QRS model is the result of sufficiently many samples.

Figure 6:
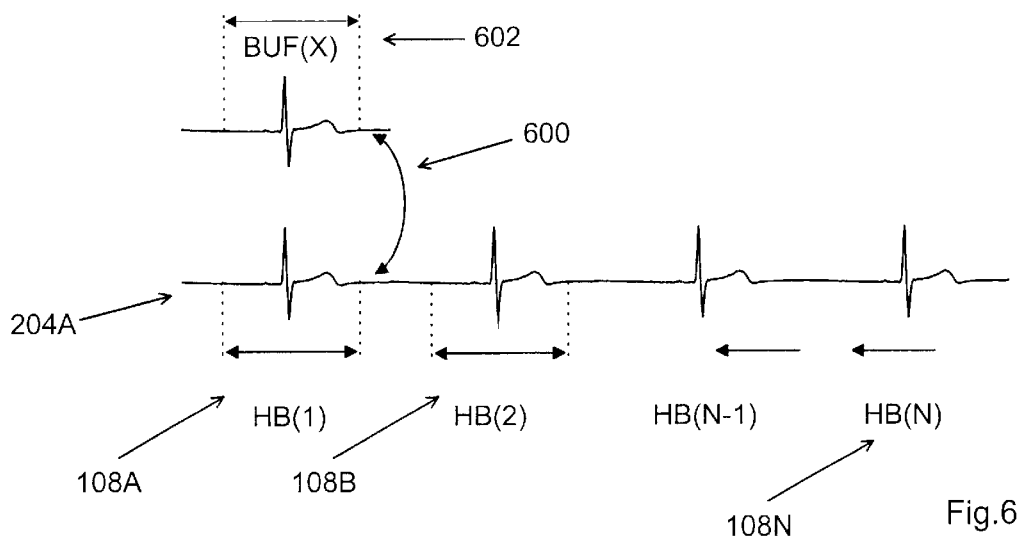
FIG. 6 shows the comparison of a measuring wave with a comparison model in a memory buffer.

FIG. 6 shows a situation during the using phase of the heart rate monitor. At this time, the device transmitting timing information from the stronger heart rate area is no longer needed. In the figure, BUF(X) 602 refers to a comparison wave model found during the training phase according to the method description of FIG. 3B. Signal sequences HB(1) to HB(N) corresponding to a heart beat can be distinguished from the heart rate signal 204A of the using phase. During the using phase, each measured measuring wave format 108A to 108N is correlated 600 with the comparison wave format 602 and always when the correlation exceeds a certain criterion, the measuring wave format is accepted as a heart beat when calculating the heart rate or another corresponding variable. The above-mentioned criterion used in comparing the measuring wave format and the comparison wave format can be, for instance, that the wave formats must correlate with each other in 70%. Instead of correlating, the comparison of the waves can be performed by any corresponding known method.

Figure 7A:
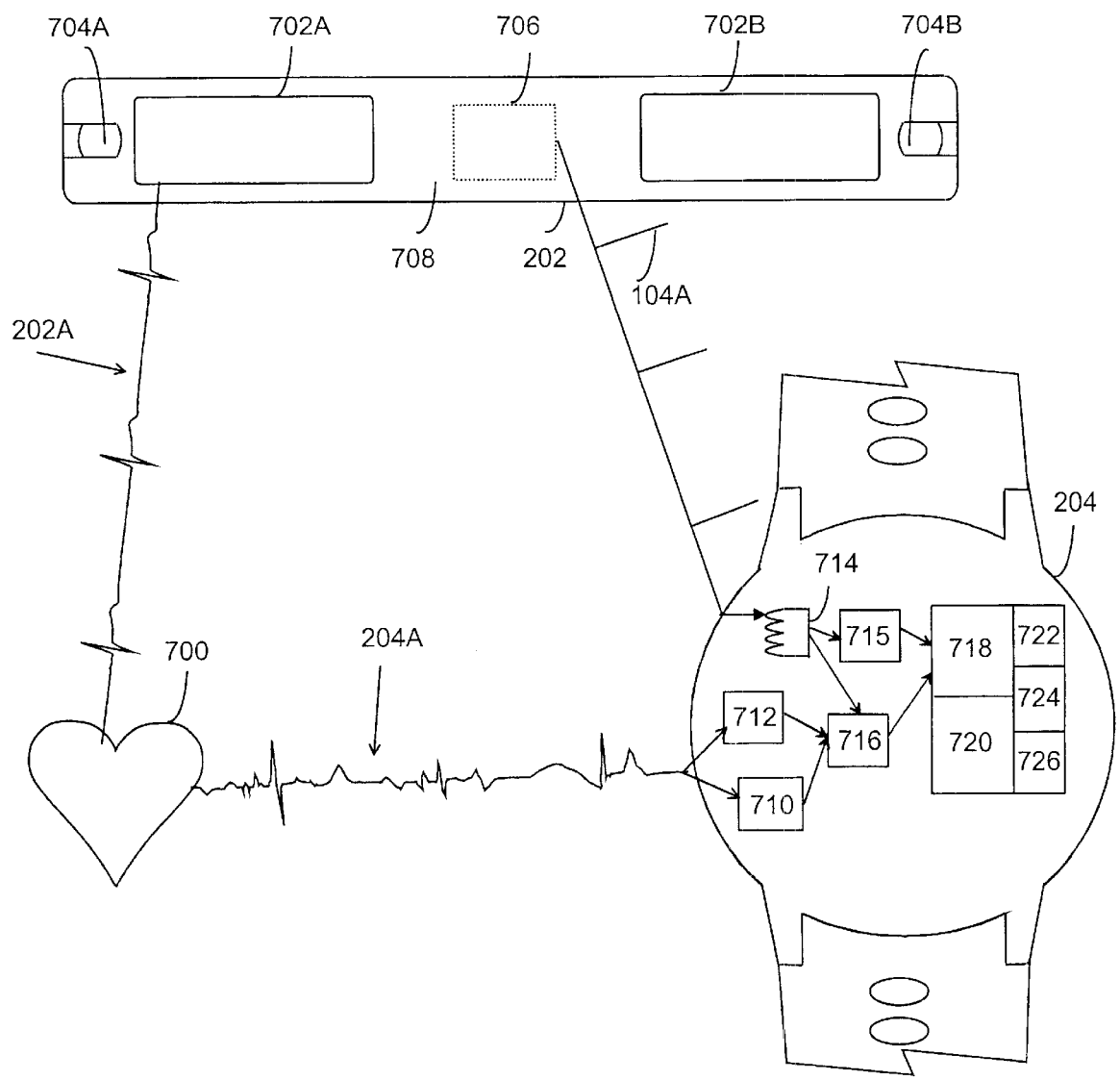
FIGS. 7A and 7B show an embodiment of a device arrangement of the invention.

FIG. 7A shows a preferred embodiment of a device arrangement of the invention. The first measuring device measuring the heart rate on the chest during the training phase is preferably a transmitter electrode belt 202 which comprises electrodes 702A and 702B. The electrode belt also comprises fastening means 704A and 704B with which the electrode belt 202 can be fastened on the chest using a flexible band which can be strapped around the body. The electrode belt 202 also comprises an electronics unit 706 whose operation is described in greater detail in FIG. 7B.

The electrode belt 202 in FIG. 7A is shown from the inside 708, i.e. from the side settling against the body, where the electrodes 702A and 702B are located. During the training phase, the electrode belt reads the heart rate signal 202A originating from the heart 700, and timing information 104A corresponding to the heart rate signal 202A is transmitted to a second measuring device belonging to the device arrangement, i.e. to a wrist receiver 204. In a solution of the invention, the wrist receiver 204 can also be called a heart rate monitor, to which a receiver for receiving external timing has been implemented as an additional feature. The heart rate signal measured by the electrode belt 202 on the chest is relatively free of interference and strong. Simultaneously with the received timing information 104A, the receiver 204 measures the heart rate signal 204A in its own measuring area, for instance the wrist. The timing information is received with receiving means 714 which is preferably a magnetic coil, for instance, for receiving electromagnetic pulses. In FIG. 7A, the signals 202A and 204A refer to the same and simultaneously measured electric signal generated by the beat of the heart 700 and measured in different locations of the body. The pulses transmitted by the heart rate transmitter belt 202 are extremely accurate and reliable and, therefore, they can be used in a wrist gauge 204 to define the time instant of the QRS complex from the EKG signal 204A which is obtained from hands and, therefore, contains interference.

The receiver unit, i.e. the wrist gauge 204, of the invention comprises means for measuring the heart rate signal 710 and 712. With pressure measurement, the means for measuring the heart rate signal 710, 712 refer to one or more pressure sensors which measure the pressure changes caused by blood circulation in a blood vessel. With optical measurement, the means for measuring the heart rate refer to a light source, such as a LED, and a receiver, such as a receiver diode. The LED illuminates the skin and tissue and the receiver diode detects the light reflecting from the skin or tissue. Since blood causes a change in light propagation, a change in blood flow, i.e. a heart beat, can be detected. In pressure measurement and optical measurement it is not possible to direct the timing information as shown in FIG. 4, for instance, to an R peak of an electrically presented heart rate signal. However, in pressure measurement and optical measurement, maximum points of the heart rate pulse can be detected in the measuring signals and they can be compared with the R peak of the EKG pulse and thus directed as described above. In electric measurement, the invention is not limited to having only two electrodes, but there may be more of them. One electrode 710 of the wrist gauge 204 is located on the back cover of the device and is thus connected to the first hand, for instance the left hand. The other electrode 712 is on top of the wrist gauge 204 and this electrode 712 is touched by a finger or fingers of the second hand, in this case the right hand. In the measurement method, detecting the heart rate is only successful when an EKG signal can be measured from both hands. The heart rate cannot be obtained by measuring an electric signal from one hand only, because measuring an electric signal requires a potential difference between the sensors 710, and 712, and this can be obtained only by measuring from both hands. The heart rate transmitter belt 202 identifies the QRS complex from the signal 202A and transmits it as an electromagnetic pulse or pulses 104A to the wrist receiver 204.

In the wrist gauge 204, the processing of the signal 204A starts from the electrodes 710 and 712. The operation of the equipment related to signal processing of the receiver 204 described in FIG. 7A is described in greater detail in FIG. 8 with respect, to the invention. Simultaneously with the processing of the EKG signal coming from the electrodes 710 and 712, the correct time of a heart beat, i.e. the time of occurrence of the QRS complex, is obtained as encoded or unencoded electromagnetic bursts. The electromagnetic pulses, i.e. the timing information 104A, are received through the receiver coil 714 and the received signal is amplified and filtered in a signal processing block 715. A processor 718 stores the timing information on memory means 720. The analogue EKG signal 204A read from the sensors 710 and 712 is processed in a signal processing unit 716, after which the signal is in digital format and the EKG signal values are stored sample by sample into a memory buffer 720. The memory buffer 720 can be a ring buffer or a shift register-type slidable storage area.

In a preferred embodiment, method steps 302 and 306 of the invention are performed by a transmitter electrode belt 302, and method steps 304 and 308 are performed by the wrist gauge 204. The method steps described in FIG. 3B are preferably performed in a processor 718 of the wrist gauge, with the exception of step 308B performed by the wrist gauge sensors 710 and 712. The equipment implementing the method steps is the processor 718 of the wrist receiver 204, which preferably implements the method steps by program. The part of the device corresponding to the method steps and implemented preferably in the processor is a detection means for detecting heart rate by means of a heart rate signal measured in the second measuring area and timing information received from the first measuring device, the detection means comprising: means for detecting heartbeat by means of a heart rate signal and timing information; means for locating from the measured heart rate information a wave peak on the basis of a received time instant; means for selecting a wave model; means for forming a combination wave of a measuring wave format and the wave model; means for replacing the wave model with the combination wave; means for repeating the method steps until the comparison wave has been found. It is also possible to implement by program in the processor and as belonging to the detection means, comparison means for correlating the measuring wave format and the comparison wave format and means for accepting the measuring wave format as a heart beat by means of the using phase of the heart rate monitor. The invention is not limited to having the above-mentioned method steps of the invention implemented in the processor 718 by program, but they can also be implemented by general or signal processors or separate logic components. FIG. 7A shows of the structures of the receiver unit 204 a display device 722 for displaying heart rate information, such as the heart rate of a person, to the user. Further, for controlling the heart rate monitor 204, there are function keys 724 and in a preferred embodiment, the use of the heart rate monitor 204 is aided by an audio signaling unit 726 for giving an alarm, for instance, when a set heart rate limit is exceeded.

Figure 7B:
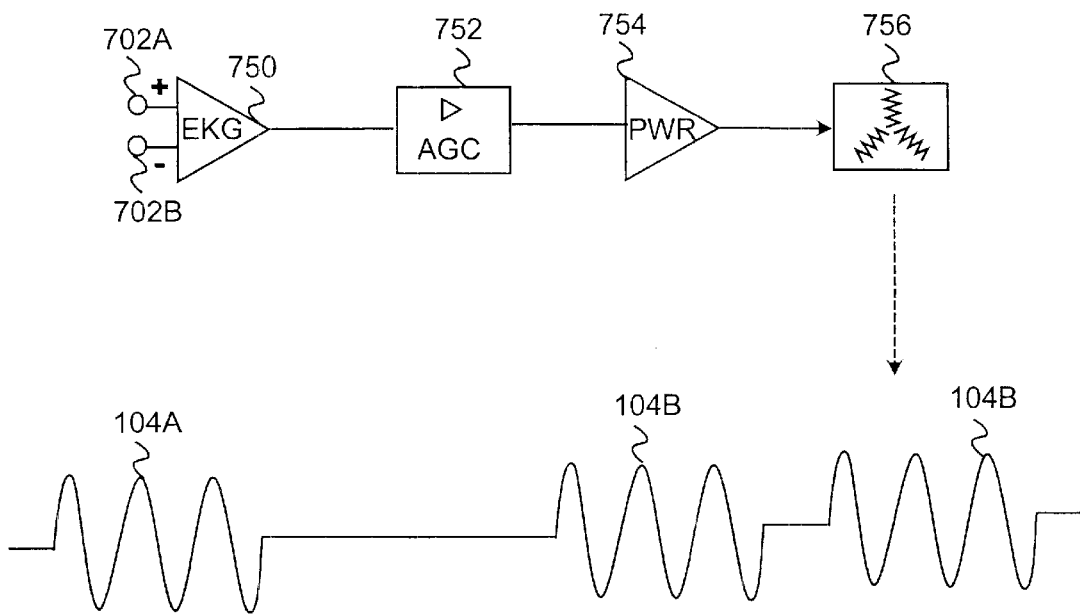

On top, FIG. 7B describes the operation of the transmitter electrode belt 202 and especially the structure of its electronics unit 706 by means of an embodiment. The bottom part of FIG. 7B shows a sample of the transmitted timing information. The electronics unit 706 of the transmitter electrode belt 202 receives heart rate information from electrodes 702A, 702B, which number at least two, but there may be more. From the electrodes 702A, 702B, the signal goes to an EKG preamplifier 750, from which the signal is transmitted through an AGC amplifier 752 and power amplifier 754 to a transmitter 756. The transmitter 756 is preferably implemented as a coil which transmits inductively the timing information 104A, 104B to the receiver. In a preferred embodiment, the timing information 104A, 104B is transmitted to the receiver in one or more analogue bursts. One 5 kHz burst 104A, for instance, corresponds to one heart beat or a group of several bursts 104B, shown in FIG. 7B as two bursts, can correspond to one heart beat. The transmission of the timing information may be done inductively or, if the transmission means are implemented in a different manner, optically or through a conductor, for instance.

Figure 8:
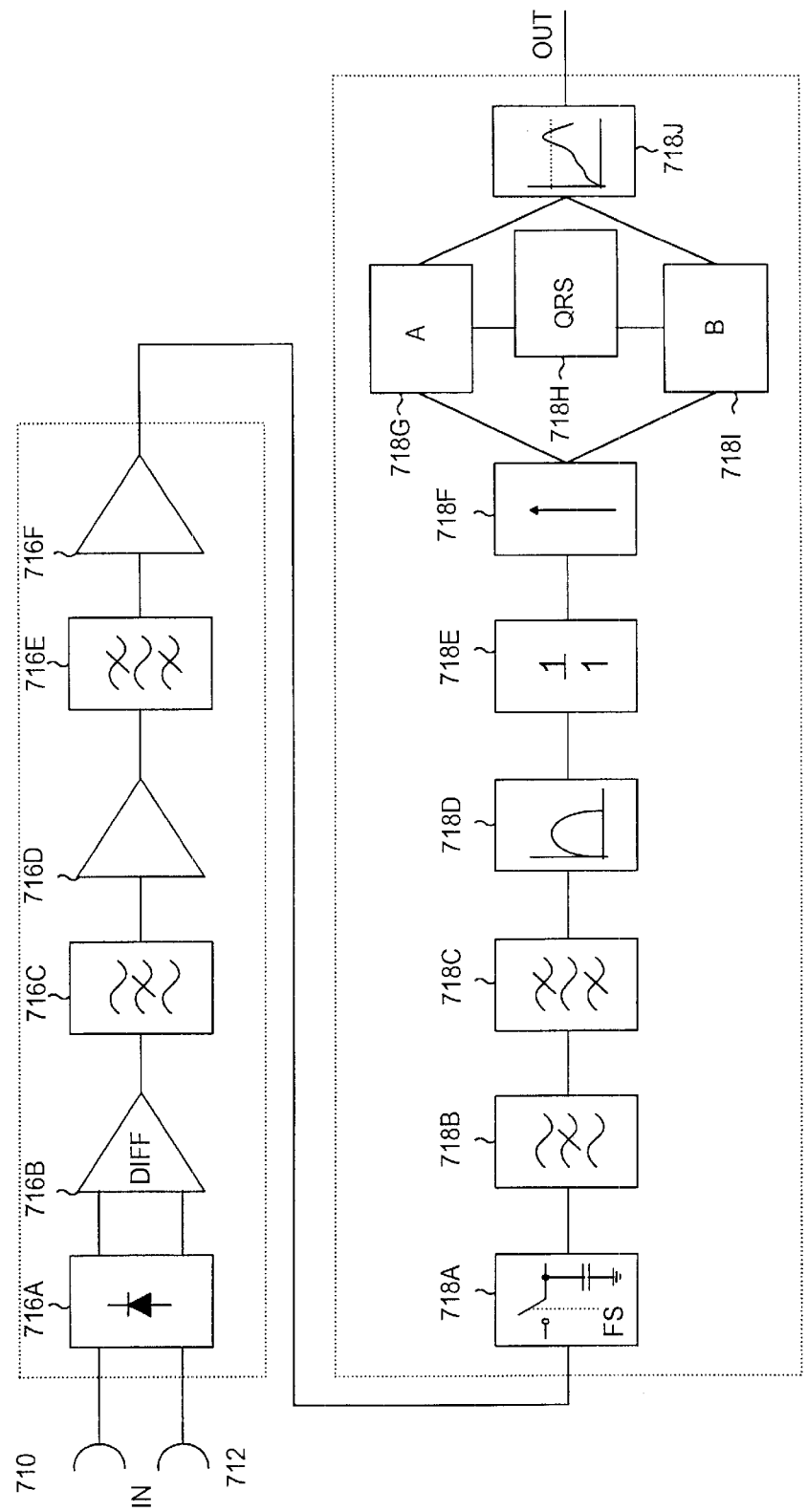
FIG. 8 shows an embodiment of a heart rate monitor of the invention.

FIG. 8 shows a preferred embodiment of the invention for the part of the wrist receiver 204 shown in FIGS. 7A. A device strapped to the wrist or an otherwise portable device should preferably be implemented so that the power source is a button battery. Usually the operating voltage is three volts. A normal clock frequency in devices like this application is 32.768 Hz, but in the using phase, a faster clock or resonator can be used. The available power dictates how heavy a program algorithm can be used in the micro-controller 718. The amplifier and filter of an EKG signal of a heart rate monitor which measures from a finger and wrist can be implemented with separate components or as an EKG amplifier integrated with silicon. Analogue electronics contains blocks 716A to 716F and the micro-controller 718 contains blocks 718A to 718J, of which 718B to 718J are implemented using a program in the micro-controller 718, for instance.

The input of the signal processing unit 716 is protected with diodes 716A against static electric discharges. A differential amplifier 716B amplifies all frequencies of a signal approximately 40 dB, for instance. A 50 Hz (or 60 Hz) interference induced from the surrounding electric cables or apparatuses in a person, i.e. the object to be measured, is amplified in an instrumentation amplifier 716B in the same proportion as the EKG signal being measured. The signal dynamics of the amplifiers is limited and the DC level drifts easily, so a high-amplitude network interference is preferably eliminated. A band-stop filter 716C eliminates the 50 Hz network interference from the signal. The filter 716C is a notch-type filter, for instance, whose medium-frequency stop-band is set at 50 Hz and at 3 dB, the bandwidth is 10 Hz. The filter 716C also attenuates the EKG signal and it is preferably amplified with an amplifier 716D. A band-pass filter 716E cuts off low- and high-frequency signal components so that the frequencies contained in the EKG signal remain.

An analogue input signal is band-limited with a low-pass filter to prevent folding. An A/D converter 718A converts the analogue signal to digital format. The processor 718 can be a general-purpose signal processor or one especially designed for signal processing. In both cases, the processor 718 runs a planned calculation algorithm and assumes that the processed signal is in numeric format. When an analogue EKG signal arrives at the A/D converter 718A of the processor 718, it has already been modified by a band-pass filter. The sampling frequency is 500 Hz (2 ms), for instance, and can at its maximum sample a signal whose highest frequency is 250 Hz (4 ms). The sampling instant in the application is determined by an internal hardware counter of the processor at 2 ms (500 Hz) intervals. In a clock interrupt routine, an A/D converter is started to cause the interruption when the conversion is finished. In an A/D converter interruption, the value of the EKG signal is read from the register and written into a FIFO buffer in the internal RAM memory of the processor.

The idea of a notch filter 718B is to eliminate a certain frequency from the signal, for instance a 50 Hz electric network interference is eliminated with the filter in question. A notch filter 718B can be implemented with several different filter structures. An integer coefficient filter can be built when $H(z)=1-Z^{-N}$ is used as the transfer function and the unit circle contains N zeros at $Z_x=e^{j2\pi x/N}$, where x=0, 1, 2, ..., (N−1) and N=5. In this case, the sampling frequency must be 500 Hz and the memory buffer at least five bytes long.

Analogue electronics do not filter low frequencies from an EKG signal sufficiently well and the filtering is improved by a digital band-pass filter 718C. The response of high frequencies caused by the borders of the QRS model of the filter 718C is attenuated by means of windowing 718D. Normalization 71E is performed on the QRS model and the incoming real-time EKG signal. Before algorithm calculation, the signal is interpolated 718F by two, i.e. the sampling rate is increased from 500 Hz to 1000 Hz to achieve a better compatibility with the QRS model.

Correlation is made with two algorithms at the same time. The first method is the A method 718G which calculates the difference in the EKG signal samples and the wave formats of the QRS model 718H. The second method is the B method 718I also based on comparing the QRS model and the measured EKG signal. The QRS model must be defined for persons whose EKG signal is being measured. Three parameters are calculated from the model and compared with the corresponding values of the EKG signal measured in real-time. Detection occurs when the differences in the parameters of the model and the measured EKG signal are minimized. The A method calculates the difference in the model and the signal, i.e. it can be called an anti-correlation or difference measurement. The B method calculates the similarity of the model and the signal. Each algorithm works better together with the other algorithm than alone. The B method provides a response on the found QRS complex earlier than the A method. The detection of the A method must occur within a time window of 60 ms, or detection is not accomplished. According to the results calculated by the algorithms, the QRS complex detection 718J occurs, if three values meet the conditions of the threshold detection. Two values are accepted if their absolute value is 70% below a long-time average. The result of the A method is zero in an ideal situation, if the EKG signal and the QRS complex match 100%. In practice, a level of 70% is enough. In an ideal situation, the error function value of the B method is also zero, but in practice, it is enough if the value is 70% below a long-time average. The third variable is an enabling function of coherence detection, whose value is zero or one. When all three conditions are met, detection occurs. After the steps described above, the time of occurrence of the QRS complex of the EKG signal measured from hands is known and the filtering algorithm of the heart rate can be performed and the display will show an exact heart rate reading.

When the monitor is taken into use, it does not have a QRS complex model in its memory. Or, when the QRS model is in the memory and a second user wants to use the monitor, the wrist gauge 204 must first be trained to identify the QRS complex format of the new user. The wrist gauge 204 waits until it receives a steady heart rate from the heart rate transmitter belt 202 and a wrist and finger contact with the sensors 710 and 712 is established. When these two conditions are met, the search for the ORS model can begin.

Even though the invention has been explained in the above with reference to examples in accordance with the accompanying drawings, it is obvious that the invention is not restricted to them but can be modified in many ways within the scope of the inventive idea disclosed in the attached claims.

What is claimed is:

1. A method of heartbeat detection, the method comprising:
   measuring a heart rate signal of a person from the person's skin in a first measuring area,
   measuring the heart rate signal of the person from the person's skin in a second measuring area simultaneously with the measurement made in the first measuring area,
   transmitting timing information formed of the heart rate signal measured in the first measuring area to a part of a device in the second measuring area, and
   detecting the heartbeat by means of the heart rate signal measured in the second measuring area and the timing information received from the first measuring area.

2. A method as claimed in claim 1, the method further comprising:
   forming from the heart rate signal of the user on the basis of the heart rate signal measured in the first measuring area, a wave format for each beat of the heart,
   transmitting a time instant corresponding to a peak of the formed wave format as timing information to the second measuring area, and
   receiving in the second measuring area the time instant of the wave format peak and locating on the basis of the time instant the corresponding wave format peak from the measuring wave format of the heart rate signal measured in the second measuring area.

3. A method as claimed in claim 1, the method further comprising:
   selecting a wave model to correspond to at least a part of a wave format of the heart rate signal formed by one heart beat,
   measuring in the second measuring area a measuring wave format generated by a heart beat,
   correlating the measuring wave format with the selected wave model and when the correlation meets a first criterion, forming a combination wave of the measuring wave format and the wave model,
   replacing the wave model with the formed combination wave,
   repeating the above-mentioned three steps until the correlation of the measuring wave format and the wave model meets a second criterion, and
   accepting the wave model as a comparison wave model.

4. A method as claimed in claim 1, the method further comprising forming in the second measuring area a measuring wave format by reading the heart rate signal measured in the second measuring area from the received time instant onward and backward until an electric signal generated by a heart beat is measured.

5. A method as claimed in claim 1, wherein in the second measuring area, the heart rate signal is substantially weaker in signal power than in the first measuring area.

6. A method as claimed in claim 1, wherein the timing information is transmitted wirelessly from the first measuring area to the second measuring area.

7. A method as claimed in claim 6, wherein the timing information corresponding to a heart beat is transmitted as one or more inductive bursts.

8. A method as claimed in claim 1, wherein the time instants corresponding to a wave format peak is the time instant corresponding to an R peak of a QRS wave format formed from the heart rate signal.

9. A method as claimed in claim 1, the method further comprising measuring the heart rate after the timing phase in the second measuring area by comparing a measuring wave format to a comparison wave format formed in the timing phase, and if the comparison meets the criterion, accepting the heart rate signal according to the measuring wave format as a heart beat when calculating the heart rate.

10. A method as claimed in claim 1, wherein the first measuring area is a person's chest.

11. A method as claimed in claim 1, wherein the second measuring area is the wrist of a person's first hand, and the second measuring area receives the heart rate signal required in forming a comparison wave format from the wrist of the first hand and from a finger of the second hand.

12. A method as claimed in claim 1, wherein the second measuring area is the wrist of a person's first hand, and the heart rate signal is, in this area, formed of the EKG signal between the wrist of the first hand and a finger of the second hand.

13. A method as claimed in claim 1, wherein the second measuring area is a person's wrist, and the heart rate signal is, in a measuring area, formed of the measuring signal of the pressure pulse of a blood vessel in the wrist.

14. A method as claimed in claim 1, wherein the second measuring area is a person's wrist and the heart rate signal is, in said measuring area, formed of an optically measured measuring signal.

15. An arrangement for heartbeat detection, wherein the arrangement comprises
   a first measuring device for measuring a heart rate signal of a person on the skin of the person in a first measuring area,
   a second measuring device for measuring the heart rate signal of a person on the skin of the person in a second measuring area simultaneously with the measurement made in the first measuring area,
   which first measuring device comprises a transmitter for transmitting timing information formed in the first measuring area to the second measuring device,
   which second measuring device comprises a receiver for receiving the timing information transmitted from the first measuring device,
   which second measuring device comprises detection means for detecting the heartbeat by means of the heart rate signal measured in the second measuring area and the timing information received from the first measuring device.

16. An arrangement as claimed in claim 15, wherein
   the transmitter of the first measuring device is arranged to transmit a time instant corresponding to a peak of the heart rate signal measured in the first measuring area to the second measuring device, and
   the receiver of the second measuring device is arranged to receive said time instant corresponding to a peak of the heart rate signal.

17. An arrangement as claimed in claim 15, wherein the detection means of the second measuring device comprises
   means for locating on the basis of a received time instant of the peak of the heart rate signal a corresponding wave peak from a measuring wave format of the heart rate signal measured in the second measuring area.

18. An arrangement as claimed in claim 15, wherein the detection means of the second measuring device comprises
   means for selecting a wave model to correspond to at least a part of the wave format of the heart rate signal formed by one heart beat,
   means for measuring a heart beat signal in the second measuring area for measuring a measuring wave format generated by a heart beat, means for correlating the measuring wave format with the selected wave model, means for forming a combination wave of the measuring wave format and wave model, if the correlation between the measuring wave format and the wave model meets a pre-set first criterion, means for replacing the wave model with the formed combination wave, means for repeating the above-mentioned three steps until the correlation between the measuring wave format and the wave model meets a second criterion, and means for accepting the wave model as a comparison wave format.

19. An arrangement as claimed in claim 15, wherein the second measuring device is adapted for measuring the heart rate signal that is substantially weaker in signal power in the second measuring area than in the first measuring area.

20. An arrangement as claimed in claim 15, wherein the transmitter is arranged to transmit the timing information wirelessly from the first measuring area to the second measuring area, and the receiver is arranged to receive the timing information transmitted wirelessly by the transmitter.

21. An arrangement as claimed in claim 15, wherein the transmitter is arranged to transmit the timing information corresponding to a heart beat as one or more inductive bursts.

22. An arrangement as claimed in claim 15, wherein the time instant corresponding to a wave peak format is the time instant corresponding to an R peak of a QRS wave format formed from the heart rate signal.

23. An arrangement as claimed in claim 15, wherein the detection means of the second measuring device comprises comparison means for comparing in the second measuring area the measuring wave format of the heart rate signal with the comparison wave format, and means for accepting the heart rate signal according to the measuring wave format as a heart beat when calculating the heart rate, if the correlation between the measuring wave format and the comparison wave format meets a pre-set criterion.

24. An arrangement as claimed in claim 15, wherein the first measuring device is arranged to measure a person's heart rate information from the skin of the person's chest.

25. An arrangement as claimed in claim 15, wherein the second measuring device is arranged to receive the heart rate signal required in forming a measuring wave format from the wrist of the first hand and from a finger of the second hand.

26. An arrangement as claimed claim 15, wherein the second measuring device is arranged to measure a heart rate signal from the EKG signal between the wrist of the first hand and the finger of the second hand of a person.

27. An arrangement as claimed in claim 15, wherein the second measuring device is arranged to measure the heart rate signal from a measuring signal of a pressure pulse of a blood vessel in a person's wrist.

28. An arrangement as claimed in claim 15, wherein the second measuring device is arranged to measure the heart rate signal from a measuring signal measured optically from a person's wrist.

29. A heart rate monitor for heartbeat detection, wherein the heart rate monitor comprises:

means for measuring a heart rate signal from a person's skin, a receiver operatively coupled to the means for measuring the heart rate signal, the receiver being adapted for receiving timing information related to a heart rate signal from at least one other means for measuring the heart rate signal, and detection means for heartbeat detection by means of the measured heart rate signal and the received timing information.

30. A heart rate monitor as claimed in claim 29, wherein the receiver is arranged to receive a time instant corresponding to a peak in a wave format formed from the heart rate signal.

31. A heart rate monitor as claimed in claim 29, wherein the detection means of the heart rate monitor comprises means for locating from a measuring signal wave format of the measured heart rate signal on the basis of a received time instant of a peak of a heart rate signal, a corresponding wave peak.

32. A heart rate monitor as claimed in claim 29, wherein the detection means of the heart rate monitor comprises means for selecting a wave model to correspond to at least a part of the wave format of the heart rate signal formed by one heart beat, means for correlating a measuring wave format measured by two or more electrodes with the selected wave model, means for forming a combination wave of the measuring wave format and wave model, if the correlation between the measuring wave format and the wave model meets a pre-set first criterion, means for replacing the wave model with the formed combination wave, means for repeating the above-mentioned three steps until the correlation between the measuring wave format and the wave model meets a second criterion, and means for accepting the wave model as a comparison wave format.

33. A heart rate monitor as claimed in claim 29, wherein the receiver is arranged to receive the timing information wirelessly.

34. A heart rate monitor as claimed in claim 29, wherein the receiver is arranged to receive the timing information corresponding to a heart beat as one or more inductive bursts.

35. A heart rate monitor as claimed in claim 29, wherein the time instant corresponding to a wave format peak is the time instant corresponding to an R peak of a QRS wave format formed from the heart rate signal.

36. A heart rate monitor as claimed in claim 29, wherein the detection means of the heart rate monitor comprises means for comparing in the second measuring area the measuring wave format with a comparison wave format formed in the timing phase and if the comparison meets a criterion, accepting the heart rate signal according to a measuring wave format as a heart beat when calculating the heart rate.

37. A heart rate monitor as claimed in claim 29, wherein the heart rate monitor comprises at least two electrodes, at least one electrode being arranged to measure the heart rate signal from the wrist of a first hand and at least one electrode being arranged to measure the heart rate signal from a finger of the second hand.

38. A heart rate monitor as claimed in claim 29, wherein the heart rate monitor comprises at least one electrode arranged to measure the heart rate signal from an EKG signal between the wrist of a person's first hand and a finger of the second hand.

39. A heart rate monitor as claimed in claim 29, wherein the heart rate monitor comprises a pressure sensor which is arranged to measure the heart rate signal from a measuring signal of a pressure pulse in a blood vessel in a person's wrist.

40. A heart rate monitor as claimed in claim 29, wherein the heart rate monitor comprises a light source and a receiver which are arranged to measure the heart rate signal optically from a person's wrist.

41. A method as claimed in claim 2, the method further comprising forming in the second measuring area a measuring wave format by reading the heart rate signal measured in the second measuring area from the received time instant onward and backward until an electric signal generated by a heart beat is measured.

* * * * *

UNITED STATES PATENT AND TRADEMARK OFFICE
CERTIFICATE OF CORRECTION

PATENT NO.     : 6,553,251 B1                                                Page 1 of 1
DATED          : April 22, 2003
INVENTOR(S)    : Tapani Lähdesmäki It is certified that error appears in the above-identified patent and that said Letters Patent is hereby corrected as shown below:

Column 6,
Line 20, now reads "204A/204B:" should read -- 204A/204B --;

Column 10,
Line 61, now reads "for the ORS model" should read -- for the QRS model --;

Signed and Sealed this

Seventh Day of October, 2003

JAMES E. ROGAN
*Director of the United States Patent and Trademark Office*